United States Patent [19]

Halfon et al.

[11] Patent Number: 5,468,868
[45] Date of Patent: Nov. 21, 1995

[54] PROCESS FOR THE SELECTIVE CHLORINATION OF 4,5-DIHYDRO-1-PHENYL-1H-1,2,4-TRIAZOL-5-ONE

[75] Inventors: Marc Halfon, Cranbury, N.J.; Craig A. Polsz, Newtown, Pa.; John H. Hoare, Turnersville, N.J.

[73] Assignee: FMC Corporation, Philadelphia, Pa.

[21] Appl. No.: 168,737

[22] Filed: Dec. 16, 1993

[51] Int. Cl.$^6$ .................................... C07D 249/12
[52] U.S. Cl. ........................................ 548/263.2
[58] Field of Search ............................ 548/263.2

[56] References Cited

U.S. PATENT DOCUMENTS

| 3,591,633 | 7/1971 | Ulrich | 548/263.2 |
| 4,818,275 | 4/1989 | Theodoridis | 548/264 |
| 4,980,480 | 12/1990 | Theodoridis | 548/263.2 |

FOREIGN PATENT DOCUMENTS 0012108  6/1980  European Pat. Off. .

OTHER PUBLICATIONS

J. Am. Chem. Soc., 74, 3171 (1952) Adams & Braun.
J. Am. Chem. Soc., 74, 3033 (1952) Adams & Holmes.
Bull. Chem. Soc. Japan, 1970, 43(10), 3318 Seguchi et al.
J. Am. Chem. Soc., 83, 4605 (1961) Stock et al.
J. Am. Chem. Soc., 798, 4044 (1960), De La Mare et al.

*Primary Examiner*—Jacqueline Haley
*Attorney, Agent, or Firm*—H. Robinson Ertelt; Robert M. Kennedy

[57] ABSTRACT

This invention provides a process for optimizing the yield of a 1-(2,4-dichlorophenyl)-4,5-dihydro-1H-1,2,4-triazol-5-one by the chlorination in two steps of a 4,5-dihydro-1-phenyl-1H-1,2,4-triazol-5-one. The critical first step is the selective chlorination of the phenyl ring in the 4-position by addition of chlorine to a solution of the 4,5-dihydro-1-phenyl-1H-1,2,4-triazol-5-one in N,N-dimethylformamide. Chlorination of the product of the first step in acetic acid/water yields the 1-(2,4-dichlorophenyl)-4,5-dihydro-1H-1,2,4-triazol-5-one in high yield.

5 Claims, No Drawings

5,468,868

PROCESS FOR THE SELECTIVE CHLORINATION OF 4,5-DIHYDRO-1-PHENYL-1H-1,2,4-TRIAZOL-5-ONE

This invention relates to the selective chlorination of a phenyl ring. In particular it discloses a process by which chlorine atoms are placed in the 2- and 4-positions of the 1-phenyl group attached to a 4,5-dihydro-3 -methyl-1H-1,2,4-triazol-5-one to prepare intermediates in the preparation of herbicides of the type described in U.S. Pat. No. 4,81 8,275. The sequence in which these chlorines are attached to the molecule is important to obtain the optimum yield of the desired product. It has been found that the method of accomplishing this is highly dependent on the solvent used for the critical first chlorination, placement of the first chlorine in the 4-position. Once this has been accomplished, the conditions for the placement of the second chlorine are neither critical nor novel.

The literature reference most closely related to this invention is U.S. Pat. No. 4,980,480, which describes numerous methods of preparing compounds having this structure. However, nowhere in this patent is there any suggestion of the conditions, including chlorinating agents or solvents, required for these reactions.

U.S. Pat. No. 4,818,275, in column 5, mentions halogenation of a 2-fluorophenyltriazolinone to produce the corresponding 2-fluoro-4-halophenyltriazolinone. This order of halogenation does not give optimum yields of a 2,4-dichlorophenyl product and is avoided by the current process. At column 7, lines 26 to 28, this same patent mentions the possibility of adding two halogens to a phenyltriazolinone, but there are no specifics indicating how to do this. In lines 37 to 43 of column 7 there is suggested the chlorination of 1-(2-fluorophenyl)-4,5-dihydro-3-difluoromethyl-1,2,4-triazol- 5(1H)-one with $SO_2Cl_2$ to produce 1-(2-fluoro-4-chlorophenyl)-4,5-dihydro- 3-difluoromethyl-1,2,4-triazol-5(1H)-one. Other patents, U.S. Pat. No. 5,041,155 and U.S. Pat. No. 5,174,809, are Divisional Applications directly related to U.S. Pat. No. 4,81 8,275 and contain identical disclosures to the parent case.

The literature contains several reports of chlorinations of phenyl rings in N,N-dimethylformamide. In one of these, R. Adams and B. H. Braun, J. Am Chem. Soc., 74, 3171(1952) reported that some polychlorinated derivatives, e.g., the tetrachloro derivative of p-phenylenedibenzenesulfonamide, not previously accessible through a one-step reaction, could be made in one step with DMF as solvent. In the second instance, reported by R. Adams and R. R. Holmes, J. Am. Chem. Soc., 74, 3033-(1952), an additional component, ferric chloride, was utilized in the chlorination of 3,3'-dichlorobenzidinebenzene-sulfonamide to produce 3,3',5,5'-tetrachlorobenzidinebenzenesulfonamide. In the first case all of the available hydrogen atoms were replaced by chlorine, and in the second case a material that had proved to be difficult to chlorinate had two hydrogens replaced.

U.S. Pat. No. 3,591,633, while disclosing the use of inert aprotic polar solvents generally for the chlorination of N,N'-diphenylurea, exemplifies only DMF to produce the corresponding bis(2,4,6-trichlorophenyl)urea. European Patent Application 12,108 describes the chlorination of 2-phenoxyanisole in DMF to prepare, after cleavage of the methyl group, 2-(4-chlorophenyl)-4,5 -dichlorophenol. While the reaction selectively prepares the desired trichloro compound, the solvent appears not to be overly critical, inasmuch as the same selectivity is found with acetonitrile, methanol, or chloroform, inter alia, as solvent. None of the references shows selective monochlorination, each showing more than one chlorine atom being introduced into each molecule. In general, chlorinations in N,N-dimethylformamide are not common, since the chlorine may react with the solvent, sometimes explosively, if the temperature is not kept relatively low.

One reference, Bull. Chem. Soc. Jap. 1970, 43(10), 3318, describes the chlorination of anisole in a series of aprotic solvents, including DMF and acetonitrile and shows that the ortho/para ratio of the products is related to the dielectric constant of the solvent by showing that a decrease in the latter causes a decrease in the former in solvents with relatively high dielectric constants. Another reference, J. Am. Chem. Soc., 83, 4605 -(1961), reports a kinetic study of the relative rates of chlorination of toluene and t-butylbenzene in several solvents, including acetonitrile.

The method of carrying out the addition of the second chlorine is not novel. It may be found in a paper by P. B. D. de la Mare, I. C. Hilton, and S. Varma, J. Chem. Soc., 798, 4044(1961). This article presents a kinetic analysis of the chlorinations of aromatic molecules in mixtures of acetic acid and water and concludes that the chlorinating agent is hypochlorous acid and shows that the rate of reaction is highest in 50/50 acetic acid/water. This method of chlorination was originally used in attempts to add both the 2 and 4 chlorines in a single step.

The original attempts to prepare 1-(2,4-dichlorophenyl)-4,5-dihydro-1H -1,2,4-triazol-5-one consisted of adding gaseous chlorine to 1-phenyl-4,5 -dihydro-1H-1,2,4-triazol-5-one in a 50/50 mixture of acetic acid/water in two stages, the first in an ice/water bath, the second heated to 80° to 100° C. The results of such a first stage are shown below as Experiment 3D. (The experiment designations refer to experiments reported in detail in the Examples.) The product of Experiment 3D is the starting material for Experiment 4K.

| Exp # | GC Area Percent | | |
|---|---|---|---|
| | 2-Cl[a] | 4-Cl[b] | 2,4-Cl[c] |
| 3D | 21.5 | 72.2 | 1.6 |
| 4K | 27.4 | 1.5 | 61.9 | a 2-Cl is 1-(2-chlorophenyl)-4-difluoromethyl-4,5-dihydro-3-methyl-1H-1,2,4-triazol-5-one b 4-Cl is 1-(4-chlorophenyl)-4-difluoromethyl-4,5-dihydro-3-methyl- 1H-1,2,4-triazol-5-one c 2,4-Cl is 1-(2,4-dichlorophenyl)-4-difluoromethyl-4,5-dihydro-3 -methyl-1H-1,2,4-triazol-5-one It can be seen that the yield of the desired 2,4-product is very low in the first stage, and that the good yield obtained in the second stage was apparently derived from the 4-chloro compound, since the 2-chloro remains substantially unchanged. (The somewhat higher relative content of the 2-chloro may be explained by the formation of by-products that do not show up on GC.) Accordingly, to optimize the yield of the desired product it is desirable to maximize the formation of the 4-chloro product while minimizing the formation of the 2-chloro product.

The process of this invention is shown by the following reaction sequence:

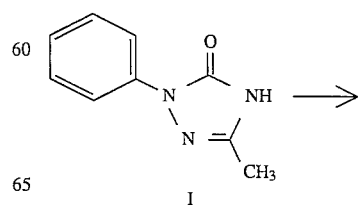

I

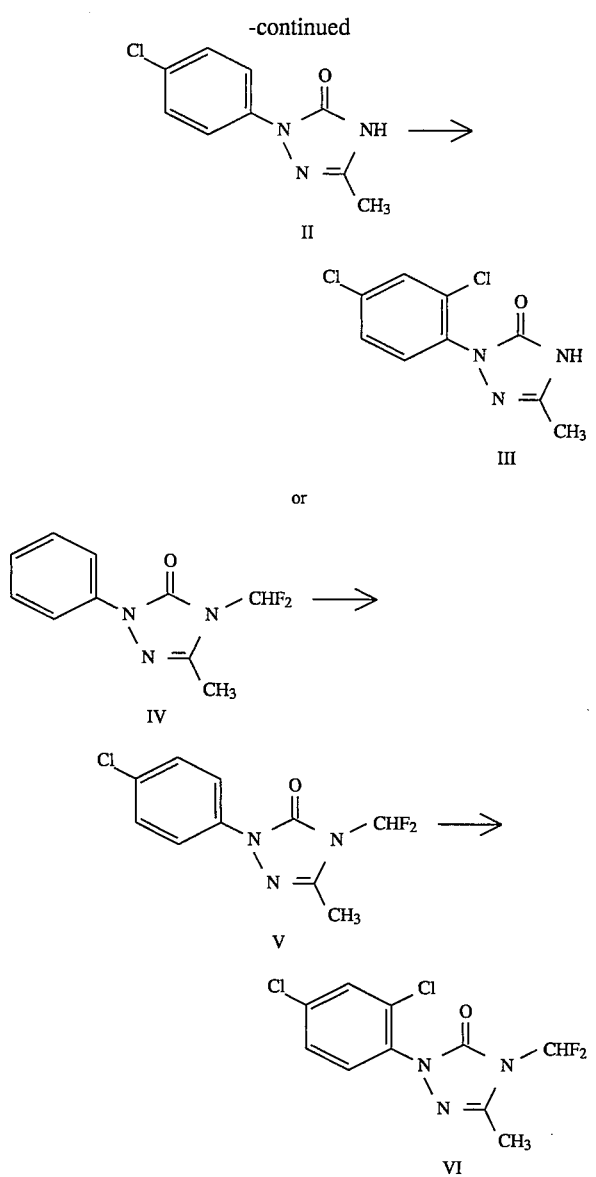

The first step of this process is the selective chlorination of I or IV to produce II or V, respectively, as shown above. The three solvents which have been identified as being especially useful for this process are N,N-dimethylformamide, N,N-dimethylacetamide, and acetonitrile. Of these three, the preferred one, particularly for the preparation of V, is N,N-dimethylformamide, because it is used in the prior difluoromethylation step to produce IV. Tables 1 and 2 give data for screening experiments on the conversion of IV to V, Table 1 on a small scale, Table 2 on a larger scale. The larger scale runs are thought to be more reliable than those on a smaller scale owing to the difficulty in controlling the amount and the rate of addition of chlorine being introduced in the small scale runs. (Examples 1 and 2 describe the runs reported in Tables 1 and 2, respectively.) Acetonitrile does not appear to have been as good a solvent in the small scale experiment as it was later shown to be in large scale trials. Example 3 and Table 3 show that the process is also effective for the chlorination of I to produce II.

The temperature range in which the first chlorination has been run is normally 0°–25° C. All of the reactions in Table 1 were run at 0° C. Those shown in Table 2 were run at 20°–25° C. with the exception of one occasion when a temperature of 76° C. was reached during an exotherm, and no significant yield loss was observed. Room temperature chlorination is preferred. (For the purpose of this application room temperature is defined as 15° to 30° C.) Either the periodic injection of chlorine or the steady bubbling of this gas into the reaction mixture is preferred to the rapid addition of all of the chlorine initially. Concentrations of 10–20 weight percent of the triazolinone in the solvent are suitable concentrations, and most examples were run in this range, but 15% is the preferred concentration. At the conclusion of the chlorination, the solvent is removed by distillation, leaving the product ready for the second chlorination step. The product of the first chlorination, either II or V, is then suspended in an acetic acid/water mixture for the second chlorination. The stirred suspension is heated to at least 70° C. The results of such experiments for the preparation of VI, including some exploratory variations, are shown in Table 4. Avoidance of the formation of the unreactive 2-chlorophenyl compound in the first chlorination step makes possible a high yield of the desired 2,4-dichlorophenyl compound. A mixture of DMF and water is clearly a poor solvent for the second chlorination. While good results are achieved at ratios of acetic acid/water of 4:1 to 1:9, clearly the maximum yield occurs at a ratio of 1:1. Table 5 shows the chlorination of II to yield III.

EXAMPLE 1

SMALL SCALE EVALUATIONS OF DIFFERENT SOLVENTS AS CHLORINATION MEDIA FOR THE SELECTIVE CHLORINATION OF 4 -DIFLUOROMETHYL-4,5-DIHYDRO-3-METHYL-1H-1,2,4-TRIAZOL-5-ONE TO 1-(4-CHLOROPHENYL)-4-DIFLUOROMETHYL-4,5-DIHYDRO-3 -METHYL-1H-1,2,4-TRIAZOL-5-ONE

In a 25 mL flask fitted with a magnetic stirrer, a condenser, and a gas dispersion tube were placed 0.50 g (0.0022 mole) of 4-difluoromethyl-4,5 -dihydro-3-methyl-1-phenyl-1H-1, 2,4-triazol-5-one and 10 mL of the solvent selected for the experiment. The flask was then cooled to 0° C. with an ice/water bath, and the addition of chlorine was begun. This addition was accomplished by periodically, usually at 15 minute intervals, filling a syringe with 20 mL of gaseous chlorine, which was then injected into the reaction mixture. The period required for this addition was 1–2 hours. The pressure of the chlorine gas was assumed to be one atmosphere for purposes of calculating the chlorine actually being added to the reaction mixture. Just prior to the addition of more chlorine, a sample of the reaction mixture was removed and analyzed by gas chromatography to determine the extent to which chlorination had taken place, as well as the composition of the sample. (While chlorine in excess of the stoichiometric amount was added to all reactions, it should be noted that unduly prolonged exposure to excess chlorine can result in the formation of unwanted by-products and a consequent reduction in yield. As the amount of starting material remaining in the reaction mixture approaches 0.1% of the original charge, the formation of by-products begins to increase significantly. Accordingly, it is advisable to monitor the course of the reaction and stop the addition of chlorine before this point is reached.) After the reaction was complete, the unreacted chlorine was sparged from the reaction mixture with nitrogen gas. All GC results in this series of experiments are reported as area percents and are not corrected for response factors. An NMR analysis of the product was made to determine the amount of by-products, including 1 -(1,2,4,4-tetrachloro-2,5-cyclohexadienyl)-4-difluoromethyl-4,5-dihydro-3 -methyl-1H-1, 2,4-triazol-5-one, either not detectable or not identified by gas chromatography. The final results of these chlorinations are reported in Table 1.

EXAMPLE 2

LARGER SCALE EVALUATIONS OF DIFFERENT SOLVENTS AS CHLORINATION MEDIA FOR THE SELECTIVE CHLORINATION OF 4-DIFLUOROMETHYL-4,5 DIHYDRO-3-METHYL-1-PHENYL-1H-1,2,4 -TRIAZOL-5-ONE TO 1-(4-CHLOROPHENYL)-4-DIFLUOROMETHYL-4,5 -DIHYDRO-3-METHYL-1H-1,2,4-TRIAZOL-5-ONE

In a 1 liter flask fitted with a mechanical stirrer, a gas dispersion tube, a dry ice condenser, and a thermometer were placed 113.9 g (0,438 mole) of 4-difluoromethyl-4,5 dihydro-3-methyl-1-phenyl-1H-1,2,4-triazol-5-one and 489 g of N,N-dimethylformamide. The flask was cooled to 20° C., and the addition of 55 g (0.78 mole) of chlorine gas was begun. This addition required 2.5 hours. Upon completion of the addition, two samples were removed for analysis by gas chromatography. The first sample was used to determine the composition of the reaction mixture which was shown to be 3.5% unknown, 0.4% starting material, 1.2% 1-(2-chlorophenyl)-4 -difluoromethyl-4,5-dihydro-3-methyl-1H-1,2, 4-triazol-5-one, 90.0% 1-(4 -chlorophenyl)-4-difluoromethyl-4,5-dihydro-3-methyl-1H-1,2,4-triazol-5-one, and <0.02% 1-(2,4-dichlorophenyl)-4-difluoromethyl-4,5-dihydro-3-methyl- 1H-1,2,4-triazol-5-one, with the remainder being various impurities in small amounts. The second sample, to which a known amount of an internal standard was added, was used to determine the weight of the 1-(4 -chlorophenyl)-4-difluoromethyl-4,5-dihydro-3-methyl-1H-1,2,4-triazol-5-one produced, from which a yield of 97% was calculated. This particular example is included in Table 2 as Example 2F. The other examples in Table 2 were run in a similar manner and at 20° C., unless stated otherwise. The yield reported for Example 2G is for the product of the second chlorination step.

EXAMPLE 3

SMALL SCALE EVALUATIONS OF DIFFERENT SOLVENTS AS CHLORINATION MEDIA FOR THE SELECTIVE CHLORINATION OF 4,5 -DIHYDRO-3-METHYL-1-PHENYL-1H-1,2,4- TRIAZOL-5-ONE TO 1-(4 -CHLOROPHENYL)-4,5-DIHYDRO-3-METHYL- 1H-1,2,4-TRIAZOL-5-ONE

In a 250 mL flask cooled by an ice/water bath and fitted with a gas inlet tube, a dry ice condenser, and a magnetic stirring bar were placed 20.0 g (0.114 mole) of 4,5-dihydro-3-methyl-1-phenyl-1H-1,2,4-triazol-5-one and 200 mL of N,N-dimethylformamide. Chlorine was bubbled into the reaction mixture for 45 minutes. During the addition of chlorine the temperature of the reaction rose from 0° C. to 12° C. Gas chromatographic analysis of the reaction mixture provided the following composition (GC area percent): 5.6% 1-(2-chlorophenyl)-4,5-dihydro-3-methyl-1H-1,2,4-triazol-5-one and 94.4% 1-(4-chlorophenyl)-4,5-dihydro-3-methyl-1H-1,2,4-triazol-5-one. A gas chromatographic weight/weight analysis using an internal standard indicated that the actual yield was 93%. This particular reaction is Example 3H in Table 3, which presents additional examples run in the same manner.

EXAMPLE 4

CHLORINATIONS OF 1-(4-CHLOROPHENYL)-4-DIFLUOROMETHYL- 3-METHYL-1H-1,2,4-TRIAZOL-5-ONE TO PREPARE 1-(2,4-DICHLOROPHENYL)-4- DIFLUOROMETHYL-3-METHYL- 1H-1,2,4-TRIAZOL-5-ONE

In a flask fitted with a magnetic stirrer, a dry ice condenser, and a silicone septum were placed 5.03 g (0.0193 mole) of 1-(4-chlorophenyl)-4 -difluoromethyl-3-methyl-1H-1,2,4-triazol-5-one, 20 mL of acetic acid, and 20 mL of water. This mixture was heated to 100° C., and periodically during a 75 minute period a total of 1300 mL of gaseous chlorine was injected by syringe into the reaction mixture. The first injection of 500 mL of chlorine caused all solids to dissolve and the solution to become orange in color. Gas chromatographic analysis showed that the composition of the reaction mixture upon completion of the reaction was 98.9% (GC area percent) 1 -(2,4-dichlorophenyl)-4-difluoromethyl-3-methyl-1H-1,2,4-triazol-5-one. A gas chromatographic weight/weight analysis using an internal standard indicated that the actual yield was 94%. This particular reaction is Example 4G in Table 4, which presents additional examples run in the same manner. Examples 4L and 4B are anomalous in that the former resulted in no reaction and the latter required at least six times as long a reaction period as normal and still resulted in only 55% conversion.

EXAMPLE 5

CHLORINATIONS OF 1-(4-CHLOROPHENYL)-4,5-DIHYDRO- 3-METHYL-1H-1,2,4-TRIAZOL-5-ONE TO PRODUCE 1-(2,4-DICHLOROPHENYL)-4,5-DIHYDRO-3- METHYL- 1H-1,2,4-TRIAZOL-5-ONE

In a 2 liter flask were placed 100 g (0.477 mole) of 1-(4-chlorophenyl)- 4,5-dihydro-3-methyl-1H-1,2,4-triazol-5-one, 500 mL of acetic acid, and 500 mL of water. This mixture was heated to 80° C., and chlorine gas was bubbled into the solution for three hours. The amount of chlorine added to the reaction was 62 g (1.156 moles). The reaction mixture contained (GC area percent): 2.5% of 1-(2-chlorophenyl)-4,5-dihydro-3-methyl-1H-1,2,4 -triazol-5-one (an impurity present in the starting material which was 92% pure), 2.7% 1-(4-chlorophenyl)-4,5-dihydro-3-methyl-1H-1,2,4-triazol-5-one, and 91.4% 1-(2,4-dichlorophenyl)-4,5-dihydro-3-methyl-1H-1,2,4 -triazol-5-one. This particular reaction is Example 5B in Table 5. The other reactions in Table 5 were all run in a similar manner to that described above.

It will be clear to those skilled in the art that modifications can be made in the process described above without departing from the inventive concept as set forth in the following claims.

TABLE 1

| Exp # | Solvent | GC Area Percent | | | | % X[f] (NMR) |
| --- | --- | --- | --- | --- | --- | --- |
| | | S.M.[a] | Unk.[b] | 2-Cl[c] | 4-Cl[d] | 2,4-Cl[e] | |
| 1A | ODCB[g] | 2 | 17 | 2 | 76 | 3 | 43 |
| 2A | CH$_2$Cl$_2$ | 2 | 14 | 3 | 80 | 1 | 14 |
| 3A | TCE[h] | 0.4 | 25 | 2 | 68 | 5 | 25 |
| 4A | Acetic Acid | 2 | 11 | 6 | 79 | 2 | 11 |
| 5A | (CH$_3$O)$_2$CO | 5 | 24 | 0.1 | 69 | 2 | >50 |

TABLE 1-continued

| | | GC Area Percent | | | | | |
|---|---|---|---|---|---|---|---|
| Exp # | Solvent | S.M.[a] | Unk.[b] | 2-Cl[c] | 4-Cl[d] | 2,4-Cl[e] | % X[f] (NMR) |
| 6A | CH₃CN | 2 | 7 | 4 | 87 | 0.3 | 11 |
| 7A | CH₃CN[i] | 1 | 8 | 4 | 86 | 0.7 | 17 |
| 8A | C₂H₅CN | 1 | 6 | 4 | 88 | 1 | 14 |
| 9A | DMF[j] | 2 | 6 | 1 | 91 | 0 | 0 |
| 10A | DMF[i] | 2 | 6 | 1 | 91 | 0.2 | 2 |
| 11A | DMA[k] | 1 | 7 | 1 | 91 | 0.2 | 2 |
| 12A | NMP[l] | 92 | 7 | 0.1 | 1 | 0.1 | — |
| 13A | DMSO[m] | Solvent reacted rapidly with the chlorine | | | | | |

[a]S.M. is starting material, i.e., 4-difluoromethyl-4,5 dihydro-3-methyl-1-phenyl-1H-1,2,4-triazol-5-one.
[b]Unk. stands for the sum of all unidentified peaks in the GC.
[c]2-Cl is 1-(2-chlorophenyl)-4-difluoromethyl-4,5-dihydro-3-methyl-1H-1,2,4-triazol-5-one
[d]4-Cl is 1-(4-chlorophenyl)-4-difluoromethyl-4,5-dihydro-3-methyl-1H-1,2,4-triazol-5-one
[e]2,4-Cl is 1-(2,4-dichlorophenyl)-4-difluoromethyl-4,5-dihydro-3-methyl-1H-1,2,4-triazol-5-one
[f]X stands for by-products not detectable by GC.
[g]ODCB is ortho-dichlorobenzene
[h]TCE is 1,1,1-trichloroethane
[i]Reaction was run in the dark.
[j]DMF is N,N-dimethylformamide
[k]DMA is N,N-dimethylacetamide
[l]NMP is 1-methyl-2-pyrrolidinone
[m]DMSO is dimethyl sulfoxide

TABLE 2

| | Solvent | | S.M.[a] | Cl₂ | GC Area Percent | | | | Percent |
|---|---|---|---|---|---|---|---|---|---|
| Exp. # | Type | Wt (g) | Wt. (g) | Wt (g) | S.M. | Unk[b] | 2-Cl[c] | 4-Cl[d] | 2,4-Cl[e] | Yield[f] |
| 2A | CH₂Cl₂ | 248 | 52 | 18.4 | 0.9 | 2.9 | 5.3 | 69.6 | 0.6 | 82 |
| 2B | TCE[g] | 248 | 52 | 45 | 9.8 | 3.0 | 4.5 | 60.5 | 1.3 | 80 |
| 2C | HOAc[h] | 248 | 52 | 45 | 0.2 | 3.6 | 8.7 | 75.7 | 4.2 | 59 |
| 2D | 50%HOAc/50%H₂O | 85 | 17.3 | 6.1 | 4.8 | 0.8 | 23.2 | 63.8 | 2.4 | 65 |
| 2E | CH₃CN | 248 | 52 | 21.3 | 2.6 | 3.9 | 3.3 | 85.2 | 0.3 | 96 |
| 2F | DMF[i] | 489 | 113.9 | 55 | 3.5 | 0.4 | 1.2 | 90.0 | <0.02 | 97 |
| 2G | DMF | 130.9 | 29.5 | 16 | — | — | 1.6 | 8.3 | 82.7 | 77.9[j,k] |
| 2H | DMA[l] | 85 | 15 | 15.0 | 3.2 | 2.9 | 0.7 | 89.1 | 0.1 | 96 |

[a]S.M. is starting material, i.e., 4-difluoromethyl-4,5 dihydro-3-methyl-1 -phenyl-1H-1,2,4-triazol-5-one.
[b]Unk. stands for the sum of all unidentified peaks in the GC.
[c]2-Cl is 1-(2-chlorophenyl)-4-difluoromethyl-4,5-dihydro-3-methyl-1 H-1,2,4-triazol-5-one.
[d]4-Cl is 1-(4-chlorophenyl)-4-difluoromethyl-4,5-dihydro-3-methyl-1 H-1,2,4-triazol-5-one.
[e]2,4-Cl is 1-(2,4-dichlorophenyl)-4-difluoromethyl-4,5-dihydro-3-methyl-1 H-1,2,4-triazol-5-one.
[f]Yield calculated by gas chromatography of a sample to which a known weight of a standard had been added.
[g]TCE is 1,1,1-trichloroethane.
[h]Reaction run at 28–30° C.
[i]DMF is N,N-dimethylformamide.
[j]The first chlorination was run in the range 23–76° C.
[k]The yield is the yield calculated by gas chromatography after removing the DMF solvent following the first chlorination, replacing it with 50/50 HOAc/H₂O, and performing the second chlorination.
[l]DMA is N,N-dimethylacetamide.

TABLE 3

| | Solvent | | S.M.[a] | GC Area Percent | | | Percent |
|---|---|---|---|---|---|---|---|
| Exp. # | Type | mL | Wt (g) | S.M. | 2-Cl[b] | 4-Cl[c] | 2,4-Cl[d] | Yield[e] |
| 3A | HOAc[f] | 10 | 1.0 | — | 11.8 | 64.0 | 10.5 | — |
| 3B | HOAc/H₂O | 8/2 | 1.0 | — | 2.0 | 65.4 | 11.0 | — |
| 3C | HOAc/H₂O | 160/40 | 20.0 | — | 22.7 | 73.8 | 0.9 | — |
| 3D | HOAc/H₂O | 5/5 | 1.0 | — | 21.5 | 72.2 | 1.6 | — |
| 3E | HOAc/H₂O[g] | 5/5 | 1.0 | 6.3 | 17.4 | 72.4 | 3.1 | — |

TABLE 3-continued

| | Solvent | | S.M.[a] | GC Area Percent | | | Percent |
|---|---|---|---|---|---|---|---|
| Exp. # | Type | mL | Wt (g) | S.M. | 2-Cl[b] | 4-Cl[c] | 2,4-Cl[d] | Yield[e] |
| 3F | DMF[h] | 10 | 1.0 | 1.5 | 6.1 | 91.3 | 1.1 | — |
| 3G | DMF | 10 | 1.0 | 2.0 | 6.5 | 89.5 | 2.1 | — |
| 3H | DMF | 200 | 20.0 | — | 5.6 | 94.4 | — | 93 |

[a]S.M. is starting material, i.e., 4,5 dihydro-3-methyl-1-phenyl-1H-1,2,4-triazol-5-one.
[b]2-Cl is 1-(2-chlorophenyl)-4,5-dihydro-3-methyl-1H-1,2,4-triazol-5-one.
[c]4-Cl is 1-(4-chlorophenyl)-4,5-dihydro-3-methyl-1H-1,2,4-triazol-5-one.
[d]2,4-Cl is 1-(2,4-dichlorophenyl)-4,5-dihydro-3-methyl-1H-1,2,4-triazol-5-one.
[e]Yield calculated by gas chromatography of a sample to which a known weight of a standard had been added.
[f]HOAC is acetic acid.
[g]Reaction run at −20° C.
[h]DMF is N,N-dimethylformamide.

TABLE 4

| | Solvent | | S.M.[a] | Cl$_2$ | GC Area Percent | | | Percent |
|---|---|---|---|---|---|---|---|---|
| Exp. # | Type | mL | Wt (g) | (eq.) | 2-Cl[b] | 4-Cl[c] | 2,4-Cl[d] | Yield[e] |
| 4A | HOAc[f,g] | 40 | 5.03 | 2.5 | — | 5.2 | 93.0 | 81.6 |
| 4B | HOAc[h] | 4 | 0.50 | 15 | — | 32.4 | 51.8 | — |
| 4C | HOAc/H$_2$O | 80/8 | 10.0 | 2.5 | — | 3.3 | 89.1 | 87 |
| 4D | HOAc/H$_2$O | 4/0.4 | 0.50 | 10 | — | 2.0 | 95.2 | — |
| 4E | HOAc/H$_2$O | 4/0.4 | 0.50 | 10 | — | 0.0 | 92.2 | — |
| 4F | HOAc/H$_2$O | 40/8 | 5.0 | 2.5 | — | 0.1 | 93.6 | 89 |
| 4G | HOAc/H$_2$O | 20/20 | 5.03 | 3 | — | 0.0 | 98.9 | 94 |
| 4H | HOAc/H$_2$O | 100/100 | 20.0 | 4 | — | 2.1 | 97.4 | 92.5 |
| 4I | HOAc/H$_2$O | 165/165 | 30.4 | 2.5 | — | 1.9 | 95.5 | 95.5 |
| 4J | DMF/H$_2$O[i] | 4/2 | 0.50 | 25 | — | 85.4 | 13.1 | — |
| 4K | HOAc/H$_2$O[j] | 5/5 | 1.0 | — | 27.4 | 1.5 | 61.9 | |
| 4L | H$_2$O | 100 | 5.03 | >5 | — | No reaction | | |
| 4M | HOAc/H$_2$O | 54/171 | 34.2 | 5 | — | 2.5 | 84.4 | 87.5 |

[a]S.M. is starting material, i.e., 1-(4-chlorophenyl)-4-difluoromethyl-4,5-dihydro-3-methyl-1H-1,2,4-triazol-5-one.
[b]2-Cl is 1-(2-chlorophenyl)-4-difluoromethyl-4,5-dihydro-3-methyl-1H-1,2,4-triazol-5-one.
[c]4-Cl is 1-(4-chlorophenyl)-4-difluoromethyl-4,5-dihydro-3-methyl-1H-1,2,4-triazol-5-one.
[d]2,4-Cl is 1-(2,4-dichlorophenyl)-4-difluoromethyl-4,5-dihydro-3-methyl-1H-1,2,4-triazol-5-one.
[e]Yield calculated by gas chromatography of a sample to which a known weight of a standard had been added.
[f]HOAC is acetic acid.
[g]Reaction contained 0.25 equivalents of ferric chloride as the catalyst.
[h]Reaction ran for 12 hours and was 55% complete.
[i]DMF is N,N-dimethylformamide.
[j]Starting material is the reaction mixture produced in Example 3D.

TABLE 5

| | Solvent | | S.M.[a] | Cl$_2$ | GC Area Percent | | | Reaction |
|---|---|---|---|---|---|---|---|---|
| Exp. # | Type | mL | Wt (g) | (eq). | 2-Cl[b] | 4-Cl[c] | 2,4-Cl[d] | Time |
| 5A | HOAc/H$_2$O[e] | 5/5 | 1.01 | 2.5 | 3.0 | 1.9 | 90.2 | 4.6 hrs. |
| 5B | HOAc/H$_2$O | 500/500 | 100 | 2.25 | 3.9 | 2.7 | 91.4 | 3.0 hrs |
| 5C | HOAc/H$_2$O | 50/50 | 10.0 | Excess | — | 2.9 | 97.1 | 3.0 hrs |
| 5D | DMF[f] | 10 | 1.0 | 1.5 | 2.0 | 40.5 | 26.0 | 6.5 hrs |
| 5E | DMF/H$_2$O | 10/5 | 1.0 | Excess | — | 87.5 | 12.2 | 24 hrs |

[a]S.M. is starting material, i.e., 1-(4-chlorophenyl)-4,5-dihydro-3-methyl-1H-1,2,4-triazol-5-one.
[b]2-Cl is 1-(2-chlorophenyl)-4,5-dihydro-3-methyl-1H-1,2,4-triazol-5-one, present in starting material.
[c]4-Cl is 1-(4-chlorophenyl)-4,5-dihydro-3-methyl-1H-1,2,4-triazol-5-one.
[d]2,4-Cl is 1-(2,4-dichlorophenyl)-4,5-dihydro-3-methyl-1H-1,2,4-triazol-5-one.
[e]HOAC is acetic acid.
[f]DMF is N,N-dimethylformamide.

We claim:

1. A process for the selective chlorination of a 4,5-dihydro-1-phenyl-1H-1,2,4-triazol-5-one selected from 4,5-dihydro-3-methyl-1-phenyl-1H-1,2,4-triazol-5-one and 4-difluoromethyl-4,5-dihydro-3-methyl-1-phenyl-1H-1,2,4-triazol-5-one in the 4-position of the phenyl ring which comprises adding excess chlorine over a period of one to three hours to a solution of the 4,5-dihydro-1-phenyl-1H-1,2,4-triazol-5-one in a solvent selected from N,N-dimethylformamide, N,N-dimethylacetamide, and acetonitrile at a temperature in the range of 0° to 80° C. and recovering the 1-(4-chlorophenyl)-4,5-dihydro-1H-1,2,4-triazol-5-one.

2. A process of claim 1 in which the temperature is in the range of 0° to 35° C., and the solvent is N,N-dimethylformamide.

3. A process of claim 2 in which the temperature is room temperature.

4. A process for the preparation of a 1-(2,4-dichlorophenyl)-4,5-dihydro-1H-1,2,4-triazol-5-one selected from 1-(2,4-dichlorophenyl)-4,5-dihydro-3-methyl-1H-1,2,4-triazol-5-one and 1-(2,4-dichlorophenyl)-4-difluoromethyl-4,5-dihydro-3-methyl-1H-1,2,4-triazol-5-one which comprises adding excess chlorine over a period of one to three hours to a suspension of a product of claim 1, 2, or 3 in acetic acid/water, in which the ratio of acetic acid to water is in the range of 4:1 to 1:9, at a temperature in the range of about 70° to 100° C. and recovering the 1-(2,4-dichlorophenyl)-4,5-dihydro-1H-1,2,4-triazol-5-one.

5. A process of claim 4 in which the ratio of acetic acid to water is 1:1.

* * * * *